United States Patent [19]

Dorn et al.

[11] 4,423,042

[45] Dec. 27, 1983

[54] INSECTICIDAL COMPOSITIONS

[75] Inventors: Silvia Dorn, Dielsdorf; Ulrich Schwieter, Reinach, both of Switzerland

[73] Assignee: Hoffmann-La Roche Inc., Nutley, N.J.

[21] Appl. No.: 365,675

[22] Filed: Apr. 5, 1982

Related U.S. Application Data

[63] Continuation of Ser. No. 226,324, Jan. 19, 1981, abandoned.

[30] Foreign Application Priority Data

Feb. 1, 1980 [CH] Switzerland ............................ 837/80

[51] Int. Cl.³ ...................... A01N 57/16; A01N 37/34
[52] U.S. Cl. ..................................... 424/200; 424/304
[58] Field of Search ................................ 424/200, 304

[56] References Cited

U.S. PATENT DOCUMENTS

| | | | |
|---|---|---|---|
| 2,754,243 | 7/1956 | Cysin | 424/200 |
| 2,960,432 | 11/1960 | Jones et al. | 424/200 |
| 4,179,518 | 12/1979 | Felton et al. | 424/304 |

FOREIGN PATENT DOCUMENTS 1439615  6/1976  United Kingdom .

OTHER PUBLICATIONS

Roger W. Williams, *J. of Economic Entomology*, vol. 72, No. 4, 1979, pp. 583–586.

*Primary Examiner*—Delbert R. Phillips
*Assistant Examiner*—F. T. Moezie
*Attorney, Agent, or Firm*—Jon S. Saxe; George M. Gould; John J. Maitner

[57] ABSTRACT

Insecticidal compositions, and methods for their use, which comprise a combination of O,O-diethyl-O-(2-isopropyl-4-methylpyrimid-6-yl)-thionophosphoric acid ester with a pyrethroid which synergizes the insecticidal activity of the thionophosphoric acid ester.

4 Claims, No Drawings

INSECTICIDAL COMPOSITIONS

This is a continuation, of application Ser. No. 226,324 filed Jan. 19, 1981, now abandoned.

BACKGROUND OF THE INVENTION

O,O-diethyl-O-(2-isopropyl-4-methyl-pyrimid-6-yl)-thionophosphoric acid ester [Diazinon] is a known compound described, for example, in U.S. Pat. No. 2,754,243 and in Zeitschrift für Naturforschung 1953, 8b, 255–232.

Since many insects develop resistance to insecticides as, for example, to phosphoric acid esters, investigations have centered on developing compounds and processes to overcome this resistance. In the case of Diazinon, for example, compounds which would synergize the activity of Diazinon were sought. The pyrethroids are one class of compounds found to act as synergists for Diazinon. Examples of such compounds useful as synergists include:

3'-phenoxy-α'-cyanobenzyl α-isopropyl-4-chlorophenylacetate [Fenvalerat], a compound which is disclosed in DOS No. 2,335,347 and 3'-phenoxy-α'-ethynylbenzyl α-isopropyl-4-chlorophenylacetate, a compound which is disclosed in DOS No. 2,365,555.

SUMMARY OF THE INVENTION

The insecticidal compositions of this invention contain, as the active ingredient, Diazinon and a pyrethroid which synergizes the insecticidal activity of Diazinon. These insecticidal compositions are active against a wide variety of pests in houses and stables, in water and open air, on plants and animals and on materials and supplies.

DETAILED DESCRIPTION OF THE INVENTION

The present invention is directed to insecticidal compositions which contain Diazinon [O,O-diethyl-O-(2-isopropyl-4-methyl-pyrimid-6-yl)-thionophosphoric acid ester], i.e. the compound of the formula

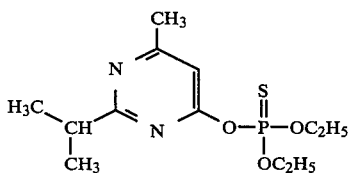

and a compound of the formula

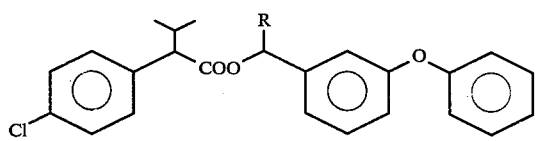

wherein R is cyano or ethynyl, and, optionally, inert carrier material.

Where R is cyano, the compound of formula II is 3'-phenoxy-α'-cyanobenzyl α-isopropyl-4-chlorophenylacetate [Fenvalerat]. Where R is ethynyl, the compound of formula II is 3'-phenoxy-α'-ethynylbenzyl α-isopropyl-4-chlorophenylacetate.

The insecticidal compositions of this invention are prepared by the usual methods for compounding, e.g. mixing Diazinon with a compound of formula II and, optionally, inert carrier material.

An especially preferred mixture comprises the compound of formula I and the compound of formula II wherein R is ethynyl. This composition has a very low toxicity to fish.

The insecticidal compositions of this invention can be used as concentrates, granulates, sprays, aerosols or wettable powders. For certain uses, it is advantageous to use the compositions in the form of emulsions, suspensions or solutions containing emulsifying or wetting agents.

The insecticidal compositions contain as inert carrier material at least one of the following materials: wetting agents, inert diluents and solvents.

The compounds of formulas I and II can be mixed with a wetting agent, with or without an inert diluent, to form a wettable powder which is soluble or dispersible in water or the compounds can be mixed with inert diluents to form a solid or pulverous product.

Inert diluents with which the compounds of formulas I and II can be admixed include solid inert media such as pulverous or finely divided solid substances, e.g. clays, sands, talc, mica, fertilizers and the like. These materials can be either dusts or material of a larger particle size.

Wetting agents, suitable for use with the compounds of formulas I and II, can be anionic, cationic or non-ionic.

Examples of anionic wetting agents include soaps, fatty sulfate esters such as sodium dodecyl sulfate, sodium octadecyl sulfate and sodium cetyl sulfate; fatty aromatic sulfates such as alkylbenzenesulfonates or butylnaphthalenesulfonates; and the more complex fatty sulfonates such as the amide condensation products of oleic acid and N-methyltaurine or the sodium sulfonate of dioctylsuccinate.

Examples of cationic wetting agents include cetyltrimethylammonium bromide and the like.

Examples of non-ionic wetting agents include, for example, condensation products of fatty acids, fatty alcohols or fatty alkyl-substituted phenols with ethylene oxide, fatty acid esters and ethers of sugars or of polyhydric alcohols, condensation products of sugars or polyhydric alcohols with ethylene oxide or block copolymers of ethylene oxide and propylene oxide.

The compounds of formulas I and II can be dissolved in a water-immiscible solvent such as, for example, a high-boiling hydrocarbon which, preferably, contains dissolved emulsifiers so that the solution acts as a self-emulsifiable oil when added to water.

The insecticidal compositions of this invention can also be used in aerosol form using, in addition to the propellant gas, carrier material comprising a co-solvent and a wetting agent. Suitable propellant gases include the polyhalogenated alkanes such as dichlorodifluoromethane.

Having regard to the amount, to be used, the following considerations apply:

The concentration of active ingredient (i.e. the compounds of formulas I and II) in the insecticidal compositions of the instant invention can vary within a wide range. For example, the active ingredient concentration can range from about 0.01 percent by weight, based on the total weight of the composition, to about 80 percent by weight (in concentrates).

The preferred ratio by weight of compounds I and II in the active ingredient is 1:1. Variations of this ratio of about 10 percent up to about 40 percent are possible. Thus, the ratio of compound I to compound II in the mixture can range from about 0.6:1 to about 1:0.6.

This invention is also concerned with a method for the treatment of animals and locus, e.g., plants and soil, subject to or subjected to attack by insects free from such attack, which method comprises applying to the animals or locus an effective amount of the insecticidal composition as defined above.

In general, the insecticidal compositions can be used in different concentrations depending on their intended end use. For example, the compositions are applied at a rate of from about 10 to about 1000 grams per hectare (g/ha) for combatting insects and pests on plants. To control ectoparasites on animals, the animals are conveniently dipped in a solution containing from about 10 to about 500 ppm of the mixture of active ingredients of formulas I and II. Alternatively, the animals can be sprayed with a solution of the same concentration.

The insecticidal compositions of this invention are active against a wide variety of insects. For example, they are active against Diptera, especially against representatives of the families Muscidae, Culicidae, Simuliidae and Calliphoridae such as, for example, *Musca* spp., *Stomoxys calcitrans, Haematobia irritans* and *Glossina morsitans; Culex* spp., *Anopheles* spp. and *Aedes* spp.; *Simulium* spp.; *Cochliomyia hominivorax, Lucilia* spp. and *Calliphora* spp.; against Orthoptera such as, for example, *Blattella germanica* and *Blatta orientalis;* against Lepidoptera such as, for example, *Adoxophyes reticulana, Ephestia kuhniella, Heliothis virescens, Laspeyresia pomonella, Ostrinia nubilalis, Plodia interpunctella, Spodoptera littoralis, Pectinophora gossypiella* and *Cnaphalocrocis medinalis;* against Coleoptera such as, for example, *Anthonomus grandis, Leptinotarsa decemlineata, Sitophilus granarius, Sitophilus oryzae, Oryzaephilus surinamensis, Oryzaephilus mercator, Tribolium confusum, Tribolium castaneum, Tribolium audax, Rhizopertha dominica, Trogoderma granarium, Lissorhoptrus oryzophilus* and *Diabrotica balteata;* against Thysanoptera such as, for example, *Thrips tabaci;* against Heteroptera such as, for example, *Dysdercus cingulatus* and *Lygus* spp.; against Homoptera such as, for example, *Aphis fabae, Laodelphax striatellus, Nephotettix virescens, Nilaparvata lugens, Myzus persicae, Trialeurodes vaporariorum, Aleurodes proletella Bemisia tabaci,* Saissetia spp., Pseudococcus spp. and *Aonidiella aurantii;* against Hymenoptera such as, for example, ants and wasps and against representatives of other orders such as, for example, silver fish and fleas; or against Acarina such as, for example, *Tetranychus* spp.; *Panonychus* spp., *Eriophyidae* and ticks.

The following Examples illustrate the invention.

EXAMPLE 1

3 days old female multiresistant flies which are especially resistant towards phosphoric acid esters are treated with an acetone solution of a mixture of Diazinon and Fenvalerat (the compound of formula II wherein R is cyano) as well as, in each case, acetone solutions of Diazinon alone and Fenvalerat alone.

To prepare these solutions, the compounds of formulae I and II were diluted several times in acetone, the dilution steps in each case corresponding to $4\sqrt{10}$.

The flies were stupefied with carbon dioxide and, for each solution, 1 μl of the dilution series was applied dorsally to the thorax of the flies. In the case of the mixture of Diazinon and Fenvalerat, the compounds were present in the composition in the weight ratio of 1:1.

The flies were incubated at 25° C. in closed plastic vessels. The drinking supply of the flies was provided by using moist cotton wool which was introduced through the vessel covers.

Mortality was determined after 24 hours. Results are listed in the following Table:

| Solution Weight ratio Fenvalerat:Diazinon | Mortality, $LD_{50}$, μg/l | Coefficient of synergism* |
|---|---|---|
| 1:0 | 0.056 | — |
| 0.5:0.5 | 0.079 | 120 |
| 0:1 | 0.311 | — |

*The coefficient of synergism is calculated according to Sun & Johnson, J. Econ. Entomol. 53 (5), 887 (1960) on the basis of the equation $$\frac{\text{Actual toxicity index of the mixture (X)} \cdot 100}{\text{Theoretical toxicity index of the mixture (Y)}},$$

wherein $X = \dfrac{LD_{50} \text{ of Diazinon} \cdot 100}{LD_{50} \text{ of the mixture}}$ and $Y = [100 \cdot A] + \dfrac{LD_{50} \text{ of Diazinon} \cdot 100 \cdot B}{LD_{50} \text{ of Fenvalerat}}$ A being the percentage of Diazinon in the mixture and B being the percentage of Fenvalerat in the mixture.

EXAMPLE 2

This Example illustrates an emulsion concentrate containing, as the active ingredient, a mixture of a compound of formula I and a compound of formula II.

| Ingredient | g/l |
|---|---|
| Compounds of formulas I and II in the weight ratio 1:1 | 500 |
| Emulsifier mixture of calcium alkyl-arylsulfonate, alkylphenol ethoxylate and block polymerisate of propylene oxide and ethylene oxide | 50 |
| Calcium dodecylbenzenesulfonate | 25 |
| Solvent consisting of a mixture of mono-, di- and tri(lower alkyl)-benzenes | to 1000 ml. |

EXAMPLE 3

This Example illustrates an aerosol preparation containing, as the active ingredient, a mixture of a compound of formula I and a compound of formula II.

| Ingredient | % per weight |
|---|---|
| Compounds of formulas I and II in the weight ratio 1:1 | 0.2 |
| Methylene chloride | 5.0 |
| Solvent consisting of a mixture of aliphatic hydrocarbons (white spirit) of average molecular weight 156; boiling range 172°–194° C. | 14.8 |
| Propellant gas consisting of 1:1 mixture of trichlorofluoromethane and dichlorodifluoromethane | 80.0 |
|  | 100.0 |

We claim:

1. An insecticidal composition which comprises a mixture of a compound of the formula

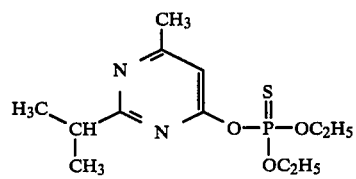

and a compound of the formula

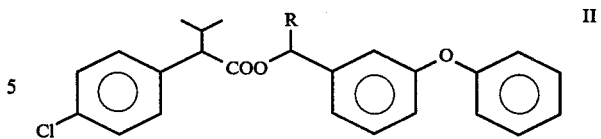

wherein R is cyano, in a ratio of I to II of from about 0.6:1 to about 1:0.6 and an inert carrier material.

2. A method for rendering a locus subject to or subjected to attack by insects free from such attack which comprises applying to the locus an insecticidally effective amount of the composition of claim 1.

3. A method of killing insects which comprises application to the insects of an insecticidally effective amount of the composition of claim 1.

4. An insecticidal composition which comprises an inert carrier material and a mixture of O,O-diethyl-O-(2-isopropyl-4-methyl-pyrimid-6-yl)-thionophosphoric acid ester and 3'-phenoxy-$\alpha^1$-cyanobenzyl-$\alpha$-isopropyl-4-chlorophenyl-acetate wherein the compounds are present in a ratio of 1:1.

* * * * *